United States Patent [19]

Rhodes et al.

[11] 4,349,429
[45] Sep. 14, 1982

[54] ELECTROPHORESIS DEVICE

[75] Inventors: Percy H. Rhodes; Robert S. Snyder, both of Huntsville, Ala.

[73] Assignee: The United States of America as represented by the Administrator of the National Aeronautics and Space Administration, Washington, D.C.

[21] Appl. No.: 254,575

[22] Filed: Apr. 16, 1981

[51] Int. Cl.³ .......................................... B01D 13/02
[52] U.S. Cl. ............................................... 204/299 R
[58] Field of Search ........... 204/299 R, 180 G, 180 R; 23/230 B

[56] References Cited

U.S. PATENT DOCUMENTS

| | | | |
|---|---|---|---|
| 4,035,377 | 7/1977 | Detroy | 204/299 R |
| 4,049,534 | 9/1977 | Posnea | 204/299 R |
| 4,111,785 | 9/1978 | Roskam | 204/299 R |
| 4,142,960 | 3/1979 | Hahn et al. | 204/299 R |
| 4,169,036 | 9/1979 | Anderson et al. | 204/299 R |

Primary Examiner—Howard S. Williams
Attorney, Agent, or Firm—Joseph H. Beumer; John R. Manning; Leon D. Wofford, Jr.

[57] ABSTRACT

An electrophoresis device is disclosed for separating cellular particles of a sample substance into fractionated streams of different cellular species wherein the device includes a casing 10 having a distribution chamber A, separation chamber B, and collection chamber C. The electrode chambers 34 are separated from the separation chamber interior 16 by means of passages 50 and 48 such that flow variations and membrane variations around the slotted portion 34a of the electrode chamber do not enduce flow perturbations into the laminar buffer curtain flowing in the separation chamber.

The cellular particles of the sample are separated under the influence of the electrical field and the separation chamber 16 and separated into streams of different cellular species. The streams of separated cells enter a partition array 52 in the collection chamber C and are fractionated and collected therein.

17 Claims, 5 Drawing Figures

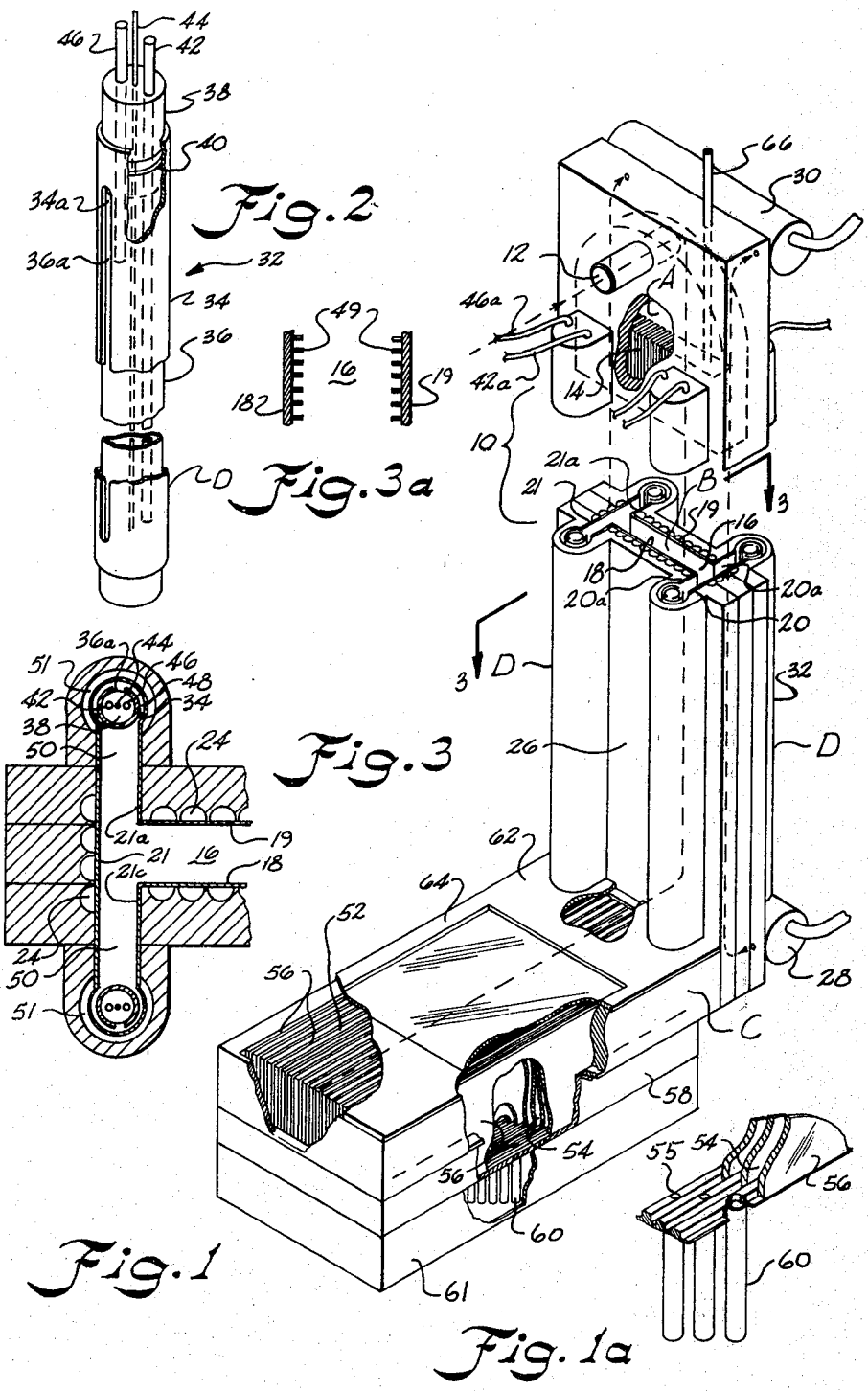

ELECTROPHORESIS DEVICE

ORIGIN OF THE INVENTION

The invention described herein was made by employees of the U.S. Government and may be manufactured and used by or for the Government for governmental purposes without the payment of any royalties thereon or therefor.

BACKGROUND OF THE INVENTION

The invention relates to the electrophoresis process wherein biological cells, colloidal particles, or macromolecules with a net electrical charge migrate and separate in a solution under the influence of an electric field and, more particularly, to a device for carrying out such a process.

The conventional continuous flow electrophoresis device is made predominantly of transparent materials, usually glass and plexiglas to facilitate observation of the separation process. The sample material being separated usually consists of a mixture of biological cells dispersed in a weak electrolyte or buffer. The chamber configuration is rectangular with electrodes on each side running down the long side of the chamber. The sample cells are inserted into the center of a flowing, thin curtain of buffer through a tube of narrower cross-section than the buffer curtain. An electrical field across the width of the chamber causes the injected sample filament to be separated into fraction streams through differential migration of the different cell species as the buffer curtain moves from one end of the chamber to the other. The electrodes are usually contained in electrode chambers which are partitioned from the separation chamber by a flat segment of dialysis membrane material. An array of collection tubes located along the end of the chamber collects the fraction bands along with all flowing buffer. The system provides for a continuous insertion, separation, and collection of injected sample and buffer.

In order to obtain optimum performance in an electrophoresis device, the fluid flow must remain essentially rectilinear even under the imposition of high voltage gradients. Present practice is to use either thin chambers and high voltage gradients or thicker chambers and very low voltage gradients. While these techniques do lower the temperature gradient in the chamber cross section thereby suppressing buoyancy induced disturbances, a large penalty is incurred in system performance. Also, current design practice is to build the chambers from transparent materials in order to observe the ongoing separation process. Transparent materials are difficult to sterilize and in general have poor thermal conductivity.

One attempt to solve this problem is the device shown in U.S. Pat. No. 3,519,549 wherein one side of the separation chamber is closed off by an electrically non-conductive plate, which is preferably transparent such as glass however since the plate is electrically non-conductive, it is also a poor thermal conductor. The other side of the separation chamber is closed off by a heat distribution plate having good thermal conductivity. However, thermal asymmetry is introduced into the chamber by providing good heat removal on one side and poor heat removal on the other. This uneven heat removal gives an asymmetrical thermal gradient in the chamber and adverse flow circulation can be set up by the unstable condition of warm fluid being at one side than at the other.

The buffer curtain that flows inside the rectangular electrophoresis chamber must be very thin, generally 0.5 to 1.5 mm, mainly because neither the fluid nor transparent chamber efficiently conduct the Joule heat out of the buffer. Since the buffer curtain is the "carrier" of the sample, the injected sample stream must be thinner than the buffer curtain. A buffer cross-flow circulation, perpendicular to the sample insertion is caused by interior walls of the chamber being charged (a phenomenon called electro-osmosis) and sample injected into the buffer near to these charged walls will be displaced by this electro-osmotic flow. The combination of electro-osmotic cross flow and Poiseuille flow of the buffer through the chamber require that the sample be inserted as a very narrow stream in the center of the buffer curtain. This, however, limits the amount of sample that can be processed in a given time interval.

The electrode chambers in conventional continuous flow electrophoresis devices are separated from the main electrophoresis chamber by dialysis or ion-exchange membranes. These membranes allow passage of the ions from electrodes to the electrophoresis chamber and inhibit passage of bubbles formed by electrolysis at the electrodes. During electrophoresis, the electrode buffer pH and conductivity drops near the cathode (negative electrode) and increases near the anode (positive electrode). These changes in ion concentration extend into the electrophoresis chamber and changes in pH of one unit and conductivity shifts of a factor of 10 have been measured in the conventional chambers near the membrane. This variation in buffer conductivity plus the normal heating of the membrane causes thermal convection and disturbance to the electrophoresis process.

The collection system for conventional continuous flow electrophoresis chambers consists of hollow tubes, either polymeric or stainless steel, that extend across the width of the chamber and partition the flow. Each element of the buffer curtain is carried by the tubes to individual glass containers that collect the buffer and separated sample. The hollow tubes necessarily have narrow bores comparable to the sample insertion tubes to give the required high resolution of separation. These narrow tubes have a propensity to clog periodically with aggregated cells and cell debris and thus disturb the laminar flow back into the chamber. Any change in flow properties of the tubes thus interferes with the consistent separation of the sample. Analysis of results is also difficult with conventional continuous flow electrophoresis systems because the containers must be individually examined to determine where the separated cells are.

Accordingly, an important objective of the present invention is to provide a continuous flow electrophoresis separation device in which the resolution and throughput is increased by utilizing proper thermal control of the chamber to suppress buoyancy induced convection along with other improvements in the sample insertion and collection system, electrode chambers, and inlet and exit flow conditions.

SUMMARY OF THE INVENTION

It has been found that the above objectives may be accomplished by an electrophoresis device which includes a distribution chamber having an inlet for the introduction of a buffer solution and a sample insertion tube for inserting a narrow sample stream containing the particles into the buffer solution and for providing enhanced resolution of separation. A separation chamber, in fluid communication with the distribution chamber, is provided, and four spaced electrode assemblies are carried adjacent the separation chamber. Each of the assemblies includes an electrode chamber having a dialysis membrane through which the electrical current flows to impress an electrical field across the separation chamber. Passages are provided through which the current flows into the separation chamber and the fluid passages provide a long path between the electrode chamber and separation chamber to effectively remove fluid and membrane variations occurring at the electrode chamber from the separation chamber. The metal enclosure walls defining the separation chamber have high thermal conductivity allowing control of the axial thermal gradient in the separation chamber by external cooling. Cooling jackets which are part of the enclosure wall convey a flow of coolant in an axial direction relative to the separation chamber. A collection chamber is provided in fluid communication with the separation chamber in which the separated particles are routed through and emerge through small orifices located in the bottom of the collection chamber.

In a preferred embodiment, the insertion tube is a thin wall, hollow quartz fiber which inserts a very narrow stream and whose thin wall effects minimize pertubation induced into the flow. The collection chamber is partitioned for collecting the separated matter deposited in a removable collection tray.

BRIEF DESCRIPTION OF THE DRAWINGS

The construction designed to carry out the invention will be hereinafter described, together with other features thereof.

The invention will be more readily understood from a reading of the following specification and by reference to the accompanying drawing(s) forming a part thereof, wherein an example of the invention is shown and wherein:

FIG. 1 is a perspective view of an electrophoresis device constructed according to the present invention with parts thereof removed and broken away;

FIG. 1a is an enlarged partial perspective view of FIG. 1 illustrating the partitioned collection chamber and tube arrangement according to the invention;

FIG. 2 is a perspective view of an electrode chamber constructed in accordance with the present invention with part is thereof removed and broken away; and FIG. 3 is a sectional view taken along line 3—3 of FIG. 1.

FIG. 3a is a cross section of the interior of the separation chamber illustrating a flow chamber and flow constricting plates according to the invention.

DESCRIPTION OF A PREFERRED EMBODIMENT

Referring now in more detail to the drawing, FIG. 1 shows a sketch of the electrophoresis device as including a casing 10 constructed from stainless steel or aluminum which includes an interior distribution chamber A, separation chamber B, and collection chamber C in fluid communication. According to the invention, buffer enters the system at 12, flows through the distribution chamber A and enters an array of conditioner tubes 14. Separation chamber B is in fluid communication with the distribution chamber A adjacently below the conditioner tubes 14 which are minute rectangular glass tubes carried face to face across the chamber that straighten the buffer flow before entering separation chamber B. Chambers A and B may be one and the same.

The separation chamber B includes enclosure wall means defined by side walls 18 and 19, end walls 20 and 21, and opposing end walls 20a and 21a. The enclosure walls of the separation chamber are constructed of a high thermal conductivity metal such as copper that allows control of the axial thermal gradient in the separation chamber B by external cooling. A micron thick coating of a polymer, selected for its electro-osmotic properties, such as epoxy or silicon, coats the surface of the copper walls exposed to the interior 16 of the separation chamber to provide electrical insulation from the buffer flowing therethrough. The copper walls may be made integral with the casing walls by any suitable means such as bonding or clamping.

The casing 10 may be made from a sandwiched plate construction clamped or bolted together using O-rings for sealing or may be machined from a piece of stock. Collection chamber C bolts onto separation chamber B.

Cooling jacket means carried adjacent the enclosure walls of the separation chamber conveys a flow of coolant in an axial direction relative to separation chamber B. As illustrated, the cooling means includes a plurality of cooling passages 24 formed in the walls 18, 19, 20 and 21 of the separation chambers. The cooling passages 24 are preferably machined in the casing 10 and are designed to transfer heat from the copper chamber walls uniformly. The copper walls are designed to a thickness to have a sufficient thermal exchange capacity for chamber B. The coolant enters the cooling passages 24 through a manifold 28 and flows up uniformly and rectilinearly to a cooling exit manifold 30 as shown by the arrows and dotted lines. Thus, cooling is uniformly provided on opposing side walls and end walls to give precise control of thermal gradients in the separation chamber. The goal is to produce no horizontal temperature gradient and a small stabilizing vertical temperature gradient of warmer fluid on top of cooler fluid in the separation chamber. Such is achieved with the cooling means illustrated. The copper plates conduct the heat out of the separation chamber and eliminate horizontal temperature gradients. Cooling fluid goes through the vertical jackets 24 adjacent the copper walls entering at the bottom and exiting at the top. The separation chamber, the cooling fluid, and copper plate tend to get warmer as the cooling fluid proceeds up through the parallel cooling jackets, thus establishing the slight stabilizing vertical thermal gradient. Buoyancy induced disturbances are virtually eliminated.

Four electrode assemblies D, which are identical, are used to impress an electrical field across the width of the separation chamber. Electrode assemblies D each include an electrode chamber 32 which includes a slotted glass tube 34 into which a section of dialysis tubing 36 is placed. The dialysis tubing provides a membrane which in the area of slot 34a allows for passage of electrical current. The dialysis membrane tube 36 is held in place by end fittings 38 which are in the form of cylindrical stopper plugs and are sealed against leakage by O-rings 40.

Rinse buffer flows into the electrode chamber through the inlet tube 42 which extends almost the length of the chamber. The rinse buffer exits the inlet tube 42 at the bottom of the chamber, flows up past the electrode 44, while removing gas bubbles and electrolysis products from the electrode and finally exits the electrode chamber through outlet tube 46 which terminates adjacent the top of the electrode chamber. Electrical current flows through the dialysis membrane 36a slot 34a, into dual channels 48 on either side of the slot and around the glass tube 34 to interconnecting channel passages 50 into the separation chamber 16. In practice, the interconnecting channel 50 is one-half the separation chamber thickness while the dual channel 48 is one-fourth the thickness of the separation channel and provide passage means for spacing and isolating membrane 36 from separation chamber B. A cooling jacket channel 51 extends about the electrode chamber. Electrode chamber B is centered in the channel 51 by means of recesses (not shown) in the electrode assembly casing D into which the end fittings 38 fit. Tubing 42a and 46a fits through a top portion of each assembly casing D and over respective tubes 42 and 46 to recirculate rinse buffer therethrough. For this purpose, a suitable recirculation pump (not shown) may be provided.

The electrode assemblies (not shown) may bolt onto the stainless steel casing using O-rings for fluid sealing and provide a uniform electrical field through the length of the separation chamber, extending from the bottom of the flow conditioner plates 14 to the beginning of the collection chamber C.

Collection chamber C is carried at a right angle adjacent the bottom of the separation chamber in fluid communication therewith and in a horizontal orientation. The collection chamber includes a partition array 52 which includes a plurality of spaced glass microsheets 56 defining separated partition spaces 54 therebetween. The thickness of each plate is approximately 0.2 mm with a spacing of 0.6 mm. The separation between plates and thickness of the plates permits higher resolution of separation and fractionation of the sample. Proceeding directly into collection tubes as in the prior art diminished resolution because the flow with separated sample must take the transition from laminar flow in a thin rectangular geometry to an array of plastic tubes embedded in some type of holder. Although the tubes could be thin walled, the two walls between each stream fraction impedes resolution. These tubes commonly plug up with aggregated sample or bubbles and the separated sample is deflected into neighboring collection tubes. Partitioning the separated sample before collecting the sample into tubes avoids the above problems.

The partition array is mounted and carried in any suitable manner in a compartment 58 which may be made integral with casing 10 of the collection chamber C in any suitable manner and may be provided with a suitable sealing ring. The depth of the compartment 58 increases the overall thickness of the collection chamber C and acts to expand the flow therein in order to reduce the flow velocity in the collection chamber. The collection region extends to the end of the collection chamber C. Each partition space 54, as it fills with cells and fluid, empties through a small port 55 in the bottom of the collection chamber. The separated cell fractions and fluid then can flow into individual glass tubes 60 for analysis of the fractions. Tubes 60 are carried in a removable collection tray 61 which may be removably attached to compartment 58 in any suitable manner such as bolts (not shown). Tubes 60 may be carried in any suitable manner such as inserted in bores drilled in a solid tray base. Since the tube diameter will necessarily be several times the partition space, these tubes will be in an offset pattern rather than arranged in a row. The upper face 62 of the collection chamber C includes a transparent glass window 64 so that the observation of the collection region is possible and fractionation of sample can be monitored.

Back-pressure on the laminarly flowing curtain buffer has previously been achieved by constricting the inside diameter of the collection tubes in conventional devices. According to the present invention, a back-pressure may be applied to the entire collection chamber without restricting the buffer flow or degrading the electrophoretic separation by pressurizing the chamber with an inert gas that doesn't impact the cells (such as argon) and this pressure will control the buffer throughput of the chamber.

In order to minimize the disturbances at the chamber side walls, flow constrictor means in the form of baffles or plates 49 may be located in the separation flow chamber B. The plates reach from the side walls into the flow region a distance of about 1.0 cm. and hence constrict the flow to the center region of the chamber (approximately 8 cm. since total chamber is 10.0 cm.). The spacing of the plates is about 1 cm. along the vertical length of the chamber. Therefore, any disturbance originating at the side walls will be confined to the volume between the plates and will not disturb flow in the central region of the chamber. The plates are critical since a thermal gradient is likely to exist in the vicinity of the side walls. The plates should be made of thin glass or other materials with a thermal conductivity near that of water in order to eliminate thermal disturbances caused by the plates. The constrictor plates, therefore, yield a constant velocity profile in the center region of the chamber where the electrophoresis will take place while confining flow disturbances to the outer regions of the chamber between the plates.

The proposed electrophoresis will separate particles based on electrophoric mobility. A sample of the particular matter enters the distribution chamber by means of an injection tube 66 at the top of the chamber which extends through the flow conditioner array 14 into the separation chamber B. Under the action of the electrical field produced by the electrode assemblies, the sample is fractionated into separate streams of particles in the separation chamber.

Upon reaching the collection chamber, each fraction will ideally enter between two separate partitions 56 in the partition array 52. Inside the collection array 52, the buffer flow rate decreases about an order of magnitude thus allowing ample time for the particles to fractionate and flow out of the bottom of the compartment 58. The buffer and separated sample exit the collection chamber through the small holes in the bottom of each partition space 54. The progress of the fractionation may be viewed through the observation window 64. During collection, the collection tray 61 may be removed and the separated sample recovered. Several trays may be required to collect all of the sample.

It has been found that by utilizing a hollow quartz optical fiber tube as the injection tube 66, the biological cells which comprise the sample can be inserted at a very narrow sample stream, and the resolution of separation by electrophoresis which depends directly upon the width of the sample insertion is enhanced. Since the diameter of most biological cells ranges from 5 to 15 microns, a 50 micron quartz fiber tube will allow these cells to pass. If the quantity of separated cells needed is more important than the resolution of separation, or the cells do not pass easily through the fiber, larger optical fibers with inside diameters ranging from 100 microns to 300 microns are commercially available and may be utilized. However, a optical fiber with a 50 micron inside diameter and wall thickness less than 20% of the diameter is commercially available as developed for the optical communications industry and work extremely well. The desired laminar flow of buffer in the separation chamber is disturbed least by the wall tubing as provided by the very thin wall of the hollow quartz fiber. In addition, the transparent fiber permits counting of the cells entering the chamber by ultraviolet radiation. Traditional metal insertion tubes will not permit this advantage of noninvasive monitoring of the sample insertion.

The design of the apparatus and selection of materials permits high pressure steam sterilization (autoclaving). In past devices, analysis of the separated biological fractions was done soon after fractionation and any contaminating bacteria or fungi were neglectable. However, the anticipated use of the present device is for placing of the separated cell fractions in culture medium to grow the cells and harvest specified protein products of the cells several days after the separation. For this application, bacteria and fungi grow significantly more rapidly than any cell species in the culture medium and the originally small population of contaminating microorganisms always become the dominant growing population in several days. The only safe and sure method of sterilization is high pressure steam temperature as high as 250° F. Thus, most plastics and tubing materials cannot be used. The proposed system uses metal and glass with some Teflon for insulation and gasketing.

Although the prior art recognizes the objective of removing Joule heat from the electrophoresis buffer layer and acknowledges that temperature gradients in the flowing buffer deform the separating sample, they do not consider that favorable temperature gradients can be achieved in the buffer layer and thereby improve the performance of the apparatus. These favorable temperature gradients can be produced only by controlling the direction and flow rate of cooling fluid in the cooling chamber 24 on each face of the separation chamber. The goal is that no horizontal temperature gradient and a small stabilizing vertical temperature gradient of warmer fluid on top of cooler fluid be established in the separation chamber. The copper plate walls conduct the heat out of the chamber most efficiently and provide the best method to eliminate horizontal temperature gradients. The cooling fluid goes through vertical channels 24 in the copper entering at the bottom and exiting at the top. As heat is withdrawn from the separation chamber, the cooling fluid and copper plate tend to get warmer as the cooling fluid proceeds up through the parallel channels, thus establishing the slight stabilizing vertical thermal gradient.

The electrophoresis chamber constructed from high conductivity metal provides a significant advantage of flow stability during electrophoresis while eliminating a lesser advantage of viewing the sample during separation. The fractionation of the sample can be observed in the collection chamber and the analysis is more meaningful. The improved thermal design of the separation chamber allows the use of higher power in the separation chamber.

The device can also be utilized to conduct continuous flow isoelectric focusing by using separate pumps and buffer for each electrode assembly. Continuous flow isoelectric focusing combines the advantages of high resolution isoelectric focusing and the collection capability of the continuous curtain flow.

Since large pressure drops do not occur in the collection array, the collection system will not degrade separation. Also, collection of the sample only will reduce the quantity of buffer needed and make buffer recycling possible. The thin wall quartz fiber tube has been found to give precise sample insertion without inducing perturbations in the flowing buffer curtain when introduced therein. The flow stability in separation chamber is enhanced.

As described previously, electrolysis products migrate through membranes, changing the pH and electrical conductivity in the buffer fluid in the separation chamber near the membrane. These changed fluid properties modify the thermal characteristics of the separation chamber and introduce an additional source of fluid disturbance. By removing the electrode membrane of the electrode chambers from the separation chamber by means of the passages 50 and 48, the problems of flow disturbances in the buffer curtain caused by variable fluid properties near the electrodes and membrane variations are substantially reduced and eliminated. The dialysis membrane, which normally provides the boundry of the separation chamber is removed by a semi-circle length of fluid (more than a centimeter as illustrated) and provides additional cooling to further eliminate horizontal thermal gradients. The electrode chamber that uses dialysis tubing instead of flat links may be easily and reliably sealed at each end to reduce the leakage problem that occurs in using flat links.

While a preferred embodiment of the invention has been described using specific terms, such description is for illustrative purposes only, and it is to be understood that changes and variations may be made without departing from the spirit or scope of the following claims.

What is claimed is:

1. An electrophoresis device for separating colloidal and macromolecular cellular particles comprising:

a distribution chamber being an inlet for the introduction of an electrolytic buffer solution;

sample insertion means for inserting a narrow sample stream containing said particles into said buffer solution;

a separation chamber in fluid communication with said distribution chamber in which said particles are separated into fraction streams of different cellular species;

enclosure wall means defining said separation chamber having high thermal conductivity to reduce horizontal thermal gradients and control the axial thermal gradient in said separation chamber by external cooling;

cooling means carried adjacent said enclosure wall means for conveying a flow of coolant in an axial direction relative to said separation chamber;

a plurality of spaced electrode assemblies carried adjacent said separation chamber, each of which includes an electrode chamber having a dialysis membrane through which the electrolytic current flows to impress an electrical field across said separation chamber;

passage means through which said current flows into said separation chamber;

a collection chamber in fluid communication with said separation chamber in which said stream of particles are fractionated and collected, and outlet means in fluid communication with said collection chamber through which said fractonated matter flows.

2. The device of claim 1 wherein said passage means spaces said electrode chamber from said separation chamber so as to effectively remove fluid and membrane variations occuring at said electrode membrane from said separation chamber to minimize flow perturbations in said buffer curtain.

3. The device set forth in claim 1 wherein said highly thermal conductive enclosure wall means include metal walls facing the interior of said separation chamber and a polymeric coating on the surface of the walls exposed to said separation chamber to provide electrical insulation from said buffer solution.

4. The device of claim 1 wherein said distribution chamber includes an array of conditioner channels through which the flow of buffer solution passes by which said flow is made parallel and distributed uniformly into the separation chamber to provide a stable buffer curtain flow through said separation chamber.

5. The device of claim 4 wherein said insertion means extends through said array of conditioner channels into said separation chamber for introduction of said sample after said buffer flow has been straightened and stabilized, said sample insertion means providing a sample stream insertion narrower than said buffer curtain so as not to introduce flow perturbations in said buffer flow.

6. The device of claim 1 wherein said insertion means includes a hollow quartz fiber optical tube.

7. The device of the claim 1 wherein said passage means includes a fluid passage surrounding said electrode chamber on either side of said membrane and an interconnecting passage connecting said circular passage and said separation chamber.

8. The device of claim 1 wherein said collection chamber includes a plurality of spaced thin upstanding plate means separating the collection chamber into minute parallel passages enhancing the fractionation of said separated particles for collection.

9. The device of claim 8 wherein said collection chamber includes a removable collection tray which carries tubes in which said separated particles may be collected and removed.

10. The device of claim 9 wherein the collection chamber includes a transparent window on the top surface thereof which allows for optical analysis of the fractionated separated particles.

11. The device of claim 1 wherein said collection chamber includes a compartment, increasing the height of said chamber facilitating an expanded flow in order to reduce the flow velocity and enhance sedimentation in said collection chamber.

12. The device of claim 1 wherein each said electrode assembly includes a tube having a vertical slot in an outer wall thereof, a dialysis tubing membrane placed within said tube, sealing means for sealing said dialysis tubing at each end of said slotted tube; a dual circular passage formed on each side of the slot of said slotted tube, and a cooling jacket surrounding said circular passage.

13. The device of claim 12 including a rinse buffer inlet formed in said sealing means including a inlet tube extending through said electrode chamber to adjacent the bottom thereof, and a rinse buffer outlet tube carried by said sealing means, and an electrode carried centrally in said chamber.

14. The device of claim 1 including flow constrictor means carried by opposing side walls of said separation chamber for confining disturbances at said side walls and preventing said disturbances from entering said buffer flow in a central region of said separation chamber.

15. The device of claim 1 wherein said distribution chamber, separation chamber, and collection chamber are all enclosed in a casing constructed from a metallic material suitable for autoclaving.

16. An electrophoresis device for separating particles of a substance into different fractions comprising:

a distribution chamber having an inlet for the introduction of an electrolytic buffer solution;

sample insertion means for inserting a narrow sample stream containing said particles into said buffer solution;

a separation chamber in which said particles are separated into fractionated streams of different cellular species;

said separation chamber being defined by highly thermal conductive metal walls facing the interior of said separation chamber having a polymeric coating on the surface thereof exposed to said separation chamber to provide electrical insulation from said buffer solution;

cooling means carried adjacent said metal walls for conveying a flow of coolant in an axial direction relative to said separation chamber;

a plurality of spaced electrode assemblies carried adjacent said separation chamber, each of which includes an electrode chamber having a dialysis membrane through which electrical current flows to impress an electrical field across said separation chamber;

passage means through which a current flows to said separation chamber, said passage means spacing said electrode chamber from said separation chamber so as to effectively remove fluid and membrane variations occurring at said electrode membrane from said separation chamber to minimize flow perturbations in said buffer curtain;

a collection chamber in fluid communication with said separation chamber including partition means by which said stream of separated particles are fractionated and collected; and outlet ports through which said buffer solution and separated fractions flow after flowing through said collection chamber.

17. An electrophoresis device for separating cellular particles in a substance comprising:

a separation chamber in which said particles are separated into said fractionated streams of different cellular species;

an inlet port introducing an electrolytic buffer solution into said separation chamber;

sample insertion means for inserting a narrow sample stream containing said particles into said buffer solution in said separation chamber;

a plurality of spaced electrode assemblies carried adjacent said separation chamber each of which includes an electrode chamber having a dialysis membrane through which an electrical current flows to impress an electrical field across said separation chamber;

passage means through which said current flows into said separation chamber;

said passage means spacing said electrode chamber from said separation chamber so as to effectively remove fluid and membrane variations occurring at said electrode membrane from said separation chamber to minimize flow perturbations in said buffer curtain;

a collection chamber in fluid communication with said separation chamber in which said stream of particles are fractionated and collected; and an outlet in fluid communication with said collection chamber.

* * * * *